United States Patent
Mohammed et al.

(10) Patent No.: US 11,766,649 B2
(45) Date of Patent: Sep. 26, 2023

(54) COATING METHOD

(71) Applicant: ASTON PARTICLE TECHNOLOGIES LIMITED, Birmingham (GB)

(72) Inventors: Professor Afzal Ur Rahman Mohammed, Birmingham (GB); Jasdip Singh Koner, Wolverhampton (GB); David Wyatt, Cambridge (GB); Eman Dahmash, Birmingham (GB)

(73) Assignee: ASTON PARTICLE TECHNOLOGIES LIMITED, Birmingham (GB)

( * ) Notice: Subject to any disclaimer, the term of this patent is extended or adjusted under 35 U.S.C. 154(b) by 0 days.

(21) Appl. No.: 16/630,542

(22) PCT Filed: Jul. 11, 2018

(86) PCT No.: PCT/EP2018/068816
§ 371 (c)(1),
(2) Date: Jan. 13, 2020

(87) PCT Pub. No.: WO2019/011998
PCT Pub. Date: Jan. 17, 2019

(65) Prior Publication Data
US 2021/0138418 A1 May 13, 2021

(30) Foreign Application Priority Data
Jul. 12, 2017 (GB) .................................. 1711233

(51) Int. Cl.
*B01J 2/00* (2006.01)
*A61K 9/00* (2006.01)
(Continued)

(52) U.S. Cl.
CPC ............. *B01J 2/006* (2013.01); *A61K 9/0075* (2013.01); *A61K 9/1635* (2013.01);
(Continued)

(58) Field of Classification Search
CPC ........................................................ B01J 2/006
See application file for complete search history.

(56) References Cited

U.S. PATENT DOCUMENTS 6,197,369 B1 * 3/2001 Watano .................... B01J 2/006
427/180
2005/0191357 A1 9/2005 Kawashima et al.

FOREIGN PATENT DOCUMENTS

EP 1498116 A1 * 1/2005 ............. A61K 31/00
EP 1498116 A1 1/2005
(Continued)

OTHER PUBLICATIONS

Pomazi, Anita, et al., Effect of Polymers for Aerolization Properties of Mannitol-Based Microcomposites Containing Meloxicam:. European Polymer Journal, vol. 49, No. 9, Mar. 24, 2013.
(Continued)

*Primary Examiner* — Tabatha L Penny
(74) *Attorney, Agent, or Firm* — Oliff PLC

(57) ABSTRACT

A process for coating carrier particles with inhalable drug guest particles, the process including providing an apparatus including a processing vessel having solid walls defining a chamber for receiving the particles and adding the particles to the chamber. Next, the cylindrical processing vessel is rotated about an axis to impart a centrifugal force of between 10 and 2100 g on the particles. Further a process coats carrier particles with guest particles, wherein the carrier particles include a material or a drug and wherein the guest particles include a solubility/dissolution controlling agent.

14 Claims, 10 Drawing Sheets

(51) Int. Cl.
*A61K 9/16* (2006.01)
*A61K 31/4166* (2006.01)
*A61K 31/5415* (2006.01)
*A61K 31/55* (2006.01)

(52) U.S. Cl.
CPC ...... *A61K 31/4166* (2013.01); *A61K 31/5415* (2013.01); *A61K 31/55* (2013.01)

(56) References Cited

FOREIGN PATENT DOCUMENTS

| | | |
|---|---|---|
| JP | 2002-507471 A | 3/2002 |
| JP | 2003-275281 A | 9/2003 |
| JP | 2012-515798 A | 7/2012 |
| JP | 2016-523823 A | 8/2016 |
| WO | 1999/048475 A1 | 9/1999 |
| WO | 2010/085780 A1 | 7/2010 |
| WO | 2014/177520 A1 | 11/2014 |
| WO | 2016/066462 A1 | 5/2016 |
| WO | WO-2016066462 A1 * | 5/2016 ................ B01J 2/12 |
| WO | 2017/047650 A1 | 3/2017 |

OTHER PUBLICATIONS

Oct. 19, 2018 International Search Report to International Application No. PCT/EP2018/068816.

Oct. 19, 2018 Written Opinion of the International Searching Authority to International Patent Application No. PCT/EP2018/068816.

Yamashita, Chikamasa. "The present state and future of dry powder inhalation system." Drug Delivery System, vol. 21, No. 4, 2006, pp. 417-425.

May 17, 2022 Office Action issued in Japanese Patent Application No. 2020-523045.

* cited by examiner

B

COATING METHOD

FIELD OF THE INVENTION

The present invention relates to a process for coating carrier particles with guest particles. In particular, the present invention relates to a process for coating carrier particles with inhalable drug guest particles. Furthermore, the present invention also relates to a process for coating carrier particles with guest particles to control solubility/dissolution and/or dissolution rate.

BACKGROUND OF THE INVENTION

It is known to coat carrier (core/host) particles with fine guest particles in order to modify the physical or chemical properties of the carrier and/or guest particle.

By use of devices that produce high shear, mechanical and compaction forces on the particles, it is possible to increase adhesion of the fine guest particles to the carrier particles to the extent that they become adsorbed onto the surface of the carrier particle. These devices must first de-agglomerate the fine guest particles and the coarser carrier particles, then mix the guest particles and the carrier particles and finally adhere the guest particles to the carrier particle using high shear, mechanical and compaction forces.

Early devices (such as the Mechanofusion high shear mill and the Hybridizer dry impactor) were capable of producing the necessary high forces but often caused attrition or even fracture of the carrier particles. Furthermore, they generated heat and thus were not suitable for use with pharmaceutical grade materials and thermo-labile particles.

U.S. Pat. No. 6,197,369B discloses a rotary fluidized bed reactor having an inner drum containing the particles which is rotated to force the particles towards the inner wall of the inner drum. The inner drum is contained within a casing which has an air inlet. Air flows radially inwards from the casing into the inner drum through slots in the inner drum wall and when the centrifugal force is balanced by the air flow, the particles are fluidized. Particle size is limited because the particles must not be small enough to pass though the slots (or through a mesh over the slots) in the inner drum wall.

WO2016/066462 discloses a process for coating carrier particles with guest particles using an apparatus having a cylindrical processing vessel rotatable about its axis with solid walls defining a chamber for receiving the particles. A hollow shaft extends within the chamber at least partly along the axis of the cylindrical processing vessel and defines a gas flow path connected to a gas inlet. The hollow shaft comprises one or more axially-extending slots or one or more axially-extending rows of apertures allowing fluid communication between the gas flow path and the chamber. After adding the particles (e.g. polymeric carrier particles and drug guest particles) to the chamber, the cylindrical processing chamber is rotated about its axis and gas is passed from the gas inlet along the gas flow path in the hollow shaft and into the chamber through the one or more axially-extending slots or one or more axially-extending rows of apertures.

In use, the collision of the particles against the inner surface of the solid walls of the processing vessel (as a result of centrifugal force) and particle fluidisation effects break down of any agglomerated guest particles and then allows exposure and adhesion of the guest particles to the carrier particles. The provision of an axially-extending hollow shaft with one or more axially-extending slots/rows of apertures allows gas to emanate in a radially-outwards direction. The radially-outwards directed gas flow is coincident with and thus reinforces the centrifugal force (and consequently increases the collision force which in turn increases the de-agglomeration, exposure and adhesion). Since the slot or row of apertures is axially-extending, the radially-outwards airflow forms at least one axially-extending sheet or "blade" of gas which increases the shear forces on the particles without any significant heat generation and without any contamination risk.

WO2016/066462 discloses use of the apparatus for formulation of oral dosage formulations of ibuprofen (a non-steroidal anti-inflammatory drug) and theophylline (an orally administered respiratory drug). For these oral dosage formulations, strong adherence between the drug and the carrier is desirable.

Delivery of drugs directly into the patient's lung for the treatment of local and systemic diseases offers a number of advantages over oral dosage formulations including: large surface area of the lungs with thin diffusion layer; proximity to circulation; and the ability to bypass the hepatic first pass effect. Furthermore, lower doses are typically used resulting in improved cost effectiveness and reduced side effects.

Drug delivery to the lungs is achieved by the aerosolisation of drug to be delivered. Micron sized particles or droplets within targeted size range are designed for delivery to the lungs. Dry powder inhalers (DPIs) are designed to deliver the drug in powder form directly to the lungs. In DPIs, the drug particles with size ranging between 1-5 µm are mixed/blended with a suitable larger carrier, typically lactose, to improve the flow properties and content uniformity. The formulation is placed into delivery systems that will be either in bulk supply (multiple dose) or quantified into unit dose delivery system, like hard gelatine capsules or blister packs. In both cases formulation reproducibility is critical. The formulation should demonstrate uniformity of content and be designed to deliver fine particles into the lower parts of the respiratory system in a consistent and reproducible pattern.

As discussed above, the apparatus described in WO2016/066462 is used to provide strong adhesion between the API and the carrier particle. Accordingly, the methods described in WO2016/066462 are unsuitable for formulating inhalable drug formulations.

SUMMARY OF THE INVENTION

In a first aspect, there is provided a process for coating carrier particles with guest particles, the process comprising:
providing an apparatus comprising a processing vessel having solid walls defining a chamber for receiving said particles, and a hollow shaft extending within said chamber at least partly along the axis of rotation of the cylindrical processing vessel, the hollow shaft defining a gas flow path connected to a gas inlet, and having one or more axially-extending slots or one or more axially-extending rows of apertures allowing fluid communication between the gas flow path and the chamber;
adding the particles to the chamber; and
rotating the cylindrical processing vessel about an axis to impart a centrifugal (G) force of between 10 and 2100 g on the particles whilst flowing gas from the gas inlet along the gas flow path in the hollow shaft and into the chamber through the one or more axially-extending slots or one or more axially-extending rows of apertures;
wherein the guest particles comprise an inhalable drug.

The present inventors have found that subjecting carrier particles and guest particles comprising an inhalable drug to a centrifugal force of between 10 and 2100 g results in the required initial deglomeration of the carrier and guest particles followed by adherence of the drug particles on the carrier particle with sufficient force that the carrier/drug particles remain associated during transport, storage and handling for incorporation into a DPI formulation. They have further found that the process results in a level of adherence between the inhalable drug and the carrier particles that allows respiratory force during use of the DPI by the patient to effect dissociation of the drug particles from the carrier particles such that the fine inhalable drug particles can enter the lower parts of the respiratory system i.e. the process results in a formulation with a maximised fine particle fraction (FPF) that provides effective delivery of the drug particles to the lower parts of the respiratory system. The process provides a cost effective, single step, high yield production process. Furthermore, the present inventors have found that the resulting particles are highly homogenous with tight content uniformity (relative standard deviation (RSD) of less than 5% and typically around 2%).

Optional features of the invention will now be set out. These are applicable singly or in any combination with any aspect of the invention.

The G force is calculated as shown below:

$$G\ force\ (g)=1.12\times10^{-5}\times R\times(RPM)^2$$

where R is radius of rotation in centimetres and RPM is the revolutions per minute.

In some embodiments the process comprises rotating the cylindrical processing vessel about an axis to impart a centrifugal (G) force of between 10-1000 g, e.g. 12-1000 g or 40-1000 g or 20 to 800 g or 80-800 g or 100 to 200 g on the particles.

The level of adherence of the guest drug particles to the host carrier particles and hence the FPF of the formulation can be controlled by controlling the centrifugal force used—the inventors have found that there is a non-linear, quadratic relationship between the FPF and the G-force with increasing $(G\text{-force})^2$ resulting in a reduction in the FPF.

In some embodiments, the process comprises rotating the cylindrical processing vessel at a speed between 10 and 4000 rpm, such as between 100-4000 rpm or 800-4000 rpm.

In some embodiments, the radius of rotation (R) i.e. the radius of the cylindrical processing vessel is between 4 and 50 cm, e.g. between 4 and 20 cm.

In some embodiments, the area/mass ratio of the combined (but not yet agglomerated guest/host particles) is between 2-20 $g/cm^2$ and/or the volume/mass ratio is 15-30 ml/g. In these embodiments, the G-force may be between 10-800 g such as between 80-800 g.

In some embodiments, the average particle size of the inhalable drug guest particle is between 1-6 micrometres (measured using a laser diffraction particle size analyser that measures particle volume).

The inhalable drug guest particles may comprise a glucocorticosteriod such as fluticasone propionate, budesonide, beclomethasone dipropionate and mometasone furoate. It may compromise a short acting Beta-2 agonist such as salbutamol, terbutaline sulphate or ipratropium bromide. It may comprise a leukotriene receptor antagonist such as theophylline, sodium cromoglycate, nedocromil sodium or ciclesonide. It may comprise a long acting Beta-2 agonist (LABA) such as formoterol fumarate, salmeterol xinafoate, indacaterol maleate, olodaterol hydrochloride or vilanterol trifenatate. It may also comprise an antimuscarinic agent such as umeclidinium bromide, aclidinium bromide, adidinium bromide, glycopyrrorium bromide (glycopyrrolate) or tiotropium bromide. It may comprise a mucolytic agent such as mannitol and dornase alfa. Anti-infective, insulin or cancer drugs are further possible options for the inhalable drug guest particles. In general, the inhalable drug guest particles can comprise any drug intended to be directly delivered to the respiratory airways for local or systemic effect.

Furthermore, the inhalable drug guest particles may include a biologic e.g. monoclonal antibody.

In some embodiments, the carrier particle size is equal or greater than 10 times the average particle size of the inhalable drug guest particles. This helps ensure good flowability of the resulting formulation.

The carrier particle size may be equal to or greater than 60 micrometres, e.g. between 60 and 190 micrometres, e.g. between 60 and 150 micrometres (measured using a laser diffraction particle size analyser that measures particle volume). The carrier particle size may be equal to or greater than 90 micrometres. Preferably it has a narrow (e.g. max 35 or 50 micron) particle size distribution.

The carrier particles may comprise lactose (e.g. α-lactose monohydrate as a reducing sugar), D-mannitol, sorbitol, erythritol, α,α-trehalose dihydrate, dextrose, glucose monohydrate, maltitol, maltose, xylitol hydroxyapatite, D-raffinose anhydrous or raffinose pentahydrate. The carrier particles may also comprise a surfactant, or a polymer (e.g. polyvinyl alcohol, polyvinylpyrrolidone, poly (lactic co glycolic acid) (PLGA)), an amino add (e.g. leucine), magnesium stearate or a cyclodextrins.

The guest material/inhalable drug concentration may be between 0.1-70% w/w of the total formulation composition.

The guest/carrier weight ratio typically varies between 1:500 (0.2%) or 1:200 (0.5%) and 1:4 (25%).

In some embodiments, the hollow shaft has a radius such that the slots/apertures are located at a relative distance of between 0 and 92% from the axis of the cylindrical processing vessel. This helps increase deglomeration.

In some embodiments, the process comprises flowing gas (e.g. nitrogen) optionally at a pressure of up to 100 psi e.g. between 20-40 psi from the gas inlet along the gas flow path in the hollow shaft and into the chamber through the one or more axially-extending slots or one or more axially-extending rows of apertures. The flow rate of the gas may be between 1 and 100 L/min, e.g. up to 75 L/min such as between 5 or 10 and 50 L/min. Use of nitrogen avoids any interaction or oxidation of the gas with the particles. The gas (e.g. nitrogen) may be heated prior to its flow along the gas flow path. The gas flow assists in breaking up agglomerates and moderates the degree of attachment of the drug particles onto the carrier particles. The rate of air flow is preferably inversely related to the G-force applied.

The apparatus may be as described in WO2016/066462.

The processing time may be between 5 and 120 minutes, preferably between 7.5 and 40 minutes and most preferably between 10 and 20 minutes. The processing time is inversely related to the G-force and rotation speed of the vessel. For example, where the G force is greater than 150 g, the processing time may be between 5 and 15 minutes and where the G force is less than 100 g, the processing time could be between 10 and 40 minutes or 10 and 30 minutes. Similarly, in some embodiments (e.g. when the carrier is Respitose SV010 with average particle size of 95-125 μm and a D90 of 160-190 μm (where D90 is the particle size of 90% of the powder)), where a rotation speed of greater than 1400 rpm is used, the processing time may be below 7 minutes but for lower rotation speeds, the processing time may be above 10 minutes.

Batch size may be between 5 g and 3000 g e.g. between 5 g and 2000 g or 20 g and 3000 g or 20 g and 2000 g e.g. between 400 g and 3000 g or 400 g and 2000 g.

In a second aspect, the present invention provides a drug formulation produced according to the process of the first aspect.

The drug formulation is for use in a dry powder inhaler.

In some embodiments, the FPF of the drug formulation is between 5 and 100% e.g. between 5 and 80%.

In a third aspect, the present invention provides a drug formulation comprising guest particles adhered to a carrier particle wherein the guest particles are an inhalable drug.

The drug formulation is for use in a dry powder inhaler.

In some embodiments, the average particle size of the inhalable drug guest particle is between 1-6 micrometres.

The inhalable drug guest particles may comprise a glucocorticosteriod such as fluticasone propionate, budesonide, beclomethasone dipropionate and mometasone furoate. It may compromise a short acting Beta-2 agonist such as salbutamol, terbutaline sulphate or ipratropium bromide. It may comprise a leukotriene receptor antagonist such as theophylline, sodium cromoglycate, nedocromil sodium or ciclesonide. It may comprise a long acting Beta-2 agonist (LABA) such as formoterol fumarate, salmeterol xinafoate, indacaterol maleate, olodaterol hydrochloride or Vilanterolvilanterol trifenatate. It may also comprise an antimuscarinic agent such as umeclidinium bromide, aclidinium bromide, adidinium bromide, glycopyrrorium bromide (glycopyrrolate) or tiotropium bromide. It may comprise a mucolytic agent such as mannitol and dornase alfa. Anti-infective, insulin or cancer drugs are further possible options for the inhalable drug guest particles. In general, the inhalable drug guest particles can comprise any drug intended to be directly delivered to the respiratory airways for local or systemic effect.

Furthermore, the inhalable drug guest particles may include a biologic e.g. monoclonal antibody.

The inhalable drug may comprise micronized particles, aggregated liposome or aggregated nanoparticles.

The inhalable drug may be thermo-labile and/or moisture sensitive and/or fracture sensitive and/or subject to contamination.

In some embodiments, the carrier particle size is equal or greater than 10 times the average particle size of the inhalable drug guest particles. This helps ensure good flowability of the resulting formulation.

The carrier particle size may be equal to or greater than 60 micrometres, e.g. between 60 and 190 micrometres, e.g. between 60 and 150 micrometres (measured using a laser diffraction particle size analyser that measures particle volume). The carrier particle size may be equal to or greater than 90 micrometres. Preferably it has a narrow (e.g. max 35 or 50 micron) particle size distribution.

The carrier particles may comprise lactose (e.g. α-lactose monohydrate as a reducing sugar), D-mannitol, sorbitol, erythritol, α,α-trehalose dihydrate, dextrose, glucose monohydrate, maltitol, maltose, xylitol hydroxyapatite, D-raffinose anhydrous or raffinose pentahydrate. The carrier particles may also comprise a surfactant, or a polymer (e.g. polyvinyl alcohol, polyvinylpyrrolidone, poly (lactic co glycolic acid) (PLGA)), an amino acid (e.g. leucine), magnesium stearate or cyclodextrins.

The carrier particles may be thermo-labile and/or moisture sensitive and/or fracture sensitive and/or subject to contamination.

In some embodiments, the FPF of the drug formulation is between 5 and 100% e.g. between 5 and 80%.

In some embodiments, the drug formulation has a content uniformity of 95-105% (RSD 0-3%).

In a fourth aspect, the present invention provides a process for coating carrier particles with guest particles, the process comprising:
providing an apparatus comprising a processing vessel having solid walls defining a chamber for receiving said particles;
adding the particles to the chamber; and
rotating the cylindrical processing vessel about an axis to impart a centrifugal (G) force on the particles;
wherein one of the carrier particles and the guest particles comprises a material having a solubility/dissolution and the other comprises a solubility/dissolution controlling agent.

The material having a solubility/dissolution may be a reduced solubility/dissolution material which encompasses: sparingly soluble materials where 1 g of the material requires 30-100 ml of solute to dissolve (at ambient temperature and pressure); slightly soluble materials where 1 g of the material requires 100-1000 ml of solute to dissolve (at ambient temperature and pressure); very slightly soluble materials where 1 g of the material may require 1000-10000 ml of solute to dissolve (at ambient temperature and pressure); insoluble materials where 1 g of material may require more than 10000 ml of solute to dissolve (at ambient temperature and pressure). In this case, the solubility/dissolution controlling agent may be a solubility/dissolution facilitator.

In other embodiments, the material having a solubility/dissolution may be a soluble material where 1 g of material dissolves in <30 ml of solute.

In a fifth aspect, the present invention provides a process for coating carrier particles with guest particles, the process comprising:
providing an apparatus comprising a processing vessel having solid walls defining a chamber for receiving said particles;
adding the particles to the chamber; and
rotating the cylindrical processing vessel about an axis to impart a centrifugal (G) force on the particles;
wherein one of the carrier particles and the guest particles comprises a drug and the other comprises a solubility/dissolution controlling agent.

The present inventors have found that subjecting guest particles and carrier particles comprising a solubility/dissolution controlling agent and a material/drug to a centrifugal force results in the required initial deglomeration of the carrier and guest particles followed by adherence of the guest particles on the carrier particle. They have further found that the process results in a hybrid particle that allows control of the solubility/dissolution (and thus the dissolution rate) of the material/drug.

Optional features of the invention will now be set out. These are applicable singly or in any combination with any aspect of the invention.

In some embodiments the process comprises rotating the cylindrical processing vessel about an axis to impart a centrifugal (G) force of between 100-1000 g, e.g. between 40-1000 g or 80 and 800 g or 100-200 g on the particles.

In some embodiments, the average particle size of the guest particle is between 0.2 and 38 micrometres (measured using a laser diffraction particle size analyser that measures particle volume).

In some embodiments, the guest particles comprise the material/drug and the carrier particles comprise the solubility/dissolution controlling agent.

In some embodiments, the carrier particles comprise the material/drug and the guest particles comprise the solubility/dissolution controlling agent.

In some embodiments, the carrier particle size is equal or greater than 5 times the average particle size of the guest particles. This helps ensure good attraction of the guest particles to the surface of the carrier particles as well as good flowability of the resulting formulation.

The carrier particle size may be equal to or greater than 50 micrometres, e.g. between 50 and 1000 micrometres or between 50 and 350 micrometres (measured using a laser diffraction particle size analyser that measures particle volume). The carrier particle size may be equal to or greater than 90 micrometres. Preferably it has a narrow (e.g. max 35 or 50 micron) particle size distribution.

The solubility/dissolution controlling agent may comprise: an anionic surfactant such as those containing sulphate, sulphonate, phosphate or carboxylate groups (e.g. sodium lauryl sulphate, docusate sodium); a cationic surfactant; a non-ionic surfactant (such as Pluronics®, polysorbates, cetomacrogol, cetostearyl alcohol, glycerol monostearate, poloxamer, stearoyl macrogol glycerides or a sorbitan alkyl ester (Span)); a zwitterionic (amphoteric) surfactant; an amino acid such as aspartic acid, glutamic acid, arginine or lysine; a sugar such as D-mannitol, sorbitol, starch or lactose; a water soluble polymer such as polyvinylpyrrolidone, polyethylene glycol, polyvinyl alcohol, hydroxypropyl methylcellulose, hydroxypropyl cellulose, poly(ethylene) oxide, methylcellulose; a disintegrant such as crospovidone, croscarmellose sodium or sodium starch glycollate; a cyclodextrin; vitamin E TPGS; ethylcellulose; or any material/a combination of material that can be used to facilitate wetting/controlled solubilisation and dissolution of a material/drug.

The drug may comprise any drug classified as a Biopharmaceutics Classification (BCS) Class I, II, III or Class IV used for oral drug delivery. Examples of BCS Class I drugs include Acetaminophen (paracetamol), Chloroquine, Diltiazem, Metoprolol, Piroxicam, Propranolol Hydrochloride, Theophylline and Verapamil. Examples of BCS Class II drugs include Amiodarone, Atorvastatin, Azithromycin, Carbamazepine, Carvedilol, Chlorpromazine, Ciprofloxacin, Ciclosporin, Danazol, Dapsone, Diclofenac, Digoxin, Erythromycin, Flurbiprofen, Glipizide, Griseofulvin, Ibuprofen, Indinavir, Indomethacin, Itraconazole. Ketoconazole, Lansoprazole, Mebendazole, Naproxen, Ofloxacin, Phenytoin, Piroxicam, Raloxifene, Ritonavir, Saquinavir, Spironolactone, Tacrolimus and Tamoxifen. Examples of BCS Class III drugs include Acyclovir, Atenolol, Captopril, Cimetidine Metformin, Neomycin B and Ranitidine. Examples of BCS Class IV drugs include Acetazolamide, Aluminium hydroxide, Amphotericin B Aprepitant, Azathioprine, Chlorothiazide, Chlorthalidone, Docetaxel, Etravirine, Famotidine, Furosemide, Hydrochlorothiazide, Indinavir, Lopinavir, Mebendazole, Methotrexate, Nelfinavir, Neomycin, Paclitaxel and Ritonavir.

Furthermore, the drug may include a biologic e.g. monoclonal antibody.

The guest particle concentration can vary between 0.5 to 70 wt % e.g. 0.5 to 40 wt %.

The carrier particles and/or guest particles may be thermo-labile and/or moisture sensitive and/or fracture sensitive and/or subject to contamination.

In some embodiments, the process comprises rotating the cylindrical processing vessel about an axis to impart a centrifugal (G) force of between 10 and 2100 g (e.g. between 12 and 2100 g) on the particles.

The G force is calculated as shown below:

$$\text{G force (g)} = 1.12 \times 10^{-5} \times R \times (RPM)^2$$

where R is radius of rotation in centimetres and RPM is the revolutions per minute.

In some embodiments, the process comprises rotating the cylindrical processing vessel about an axis to impart a centrifugal (G) force of between 10-2000 g, e.g. 40-1000 g, 80 to 800 g or 100 to 200 g on the particles.

In some embodiments, the process comprises rotating the cylindrical processing vessel at a speed between 250 and 4000 rpm, such as between 100 and 4000 rpm or 800-4000 rpm.

In some embodiments, the radius of rotation (R) i.e. the radius of the cylindrical processing vessel is between 4 and 50 cm, e.g. between 4 and 20 cm.

In some embodiments, the area/mass ratio is between 2-20 g/cm² and/or the volume/mass ratio is 15-30 ml/g. In these embodiments, the G-force may be between 80-800 g.

In some embodiments, the apparatus further comprises a hollow shaft extending within said chamber at least partly along the axis of rotation of the cylindrical processing vessel, the hollow shaft defining a gas flow path connected to a gas inlet, and having one or more axially-extending slots or one or more axially-extending rows of apertures allowing fluid communication between the gas flow path and the chamber, and the process further comprises flowing gas from the gas inlet along the gas flow path in the hollow shaft and into the chamber through the one or more axially-extending slots or one or more axially-extending rows of apertures.

In some embodiments, the hollow shaft has a radius such that the slots/apertures are located at a relative distance of between 0 and 92% from the axis of the cylindrical processing vessel. This helps increase deglomeration.

In some embodiments, the process comprises flowing gas (e.g. nitrogen) optionally at a pressure of up to 100 psi e.g. between 20-40 psi from the gas inlet along the gas flow path in the hollow shaft and into the chamber through the one or more axially-extending slots or one or more axially-extending rows of apertures. The flow rate of the gas may be between 1 and 100 L/min, e.g. up to 75 L/min such as between 5 or 10 and 50 L/min. Use of nitrogen avoids any interaction or oxidation of the gas with the particles. The gas (e.g. nitrogen) may be heated prior to its flow along the gas flow path. The gas flow assists in breaking up agglomerates and moderates the degree of attachment of the drug particles onto the carrier particles. The rate of air flow is preferably inversely related to the G-force applied.

The apparatus may be as described in WO2016/066462.

For the optimal performance of powders designed to control solubility/dissolution rate, processing time is inversely related to G-force, with powders requiring moderate to strong attachment. The higher the G-force the shorter the processing time is. Preferred processing time ranges between 10-120 minutes, e.g. 10-60 minutes. Longer processing times (e.g. up to 120 minutes) may be used with large batch size (2 or 3 kg) or when the G-force is set at the lower range of below 100 g.

The apparatus may be as described in WO2016/066462.

In a sixth aspect, the present invention provides a drug formulation produced according to the process of the fourth aspect.

The drug formulation may be for oral administration. Alternatively, it may be for an inhalable formulation, an injectable formulation or a topical formulation.

In a seventh aspect, the present invention provides a drug formulation comprising guest particles adhered to a carrier particle wherein one of the carrier particles and the guest particles is a drug and the other is a solubility/dissolution controlling agent.

The drug formulation may be for oral administration. Alternatively, it may be for an inhalable formulation, an injectable formulation or a topical formulation.

In some embodiments, the average particle size of the guest particle is between 0.2 and 38 micrometres (measured using a laser diffraction particle size analyser that measures particle volume).

In some embodiments, the carrier particle size is equal or greater than 5 times the average particle size of the solubility/dissolution guest particles. This helps ensure good attraction of the fine guest particles to the surface of the carrier particles as well as good flowability of the resulting formulation.

The carrier particle size may be equal to or greater than 50 micrometres, e.g. between 50 and 1000 micrometres or between 50 and 350 micrometres (measured using a laser diffraction particle size analyser that measures particle volume). The carrier particle size may be equal to or greater than 90 micrometres. Preferably it has a narrow (e.g. max 35 or 50 micron) particle size distribution.

The solubility/dissolution controlling agent may comprise: an anionic surfactant such as those containing sulphate, sulphonate, phosphate or carboxylate groups (e.g. sodium lauryl sulphate, docusate sodium); a cationic surfactant; a non-ionic surfactant (such as Pluronics®, polysorbates, cetomacrogol, cetostearyl alcohol, glycerol monostearate, poloxamer, stearoyl macrogol glycerides or a sorbitan alkyl ester (Span)); a zwitterionic (amphoteric) surfactant; an amino acid such as aspartic acid, glutamic acid, arginine or lysine; a sugar such as D-mannitol, sorbitol, starch or lactose; a water soluble polymer such as polyvinylpyrrolidone, polyethylene glycol, polyvinyl alcohol, hydroxypropyl methylcellulose, hydroxypropyl cellulose, poly(ethylene) oxide, methylcellulose; a disintegrant such as crospovidone, croscarmellose sodium or sodium starch glycollate; a cyclodextrin; vitamin E TPGS; ethylcellulose; or any material/a combination of material that can be used to facilitate wetting controlled solubilisation of a material/drug.

In some embodiments, the solubility/dissolution controlling agent may be micronized.

In some embodiments, the drug may be micronized.

The drug may comprise any drug classified as a Biopharmaceutics Classification (BCS) Class I, II, III or Class IV used for oral drug delivery. Examples of BCS Class I drugs include Acetaminophen (paracetamol), Chloroquine, Diltiazem, Metoprolol, Piroxicam, Propranolol Hydrochloride, Theophylline and Verapamil. Examples of BCS Class II drugs include Amiodarone, Atorvastatin, Azithromycin, Carbamazepine, Carvedilol, Chlorpromazine, Ciprofloxacin, Ciclosporin, Danazol, Dapsone, Diclofenac, Digoxin, Erythromycin, Flurbiprofen, Glipizide, Griseofulvin, Ibuprofen, Indinavir, Indomethacin, Itraconazole. Ketoconazole, Lansoprazole, Mebendazole, Naproxen, Ofloxacin, Phenytoin, Piroxicam, Raloxifene, Ritonavir, Saquinavir, Spironolactone, Tacrolimus and Tamoxifen. Examples of BCS Class III drugs include Acyclovir, Atenolol, Captopril, Cimetidine Metformin, Neomycin B and Ranitidine. Examples of BCS Class IV drugs include Acetazolamide, Aluminium hydroxide, Amphoteracin B Aprepitant, Azathioprine, Chlorothiazide, Chlorthalidone, Docetaxel, Etravirine, Famotidine, Furosemide, Hydrochlorothiazide, Indinavir, Lopinavir, Mebendazole, Methotrexate, Nelfinavir, Neomycin, Paclitaxel and Ritonavir.

Furthermore, the drug may include a biologic e.g. monoclonal antibody.

The guest particle content can vary between 0.5 to 70 wt % e.g. 0.5 to 40 wt %.

In some embodiments, the guest particles comprise the drug and the carrier particles comprise the solubility/dissolution controlling agent.

In some embodiments, the carrier particles comprise the drug and the guest particles comprise the solubility/dissolution controlling agent.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES OF THE INVENTION

Figure 1:
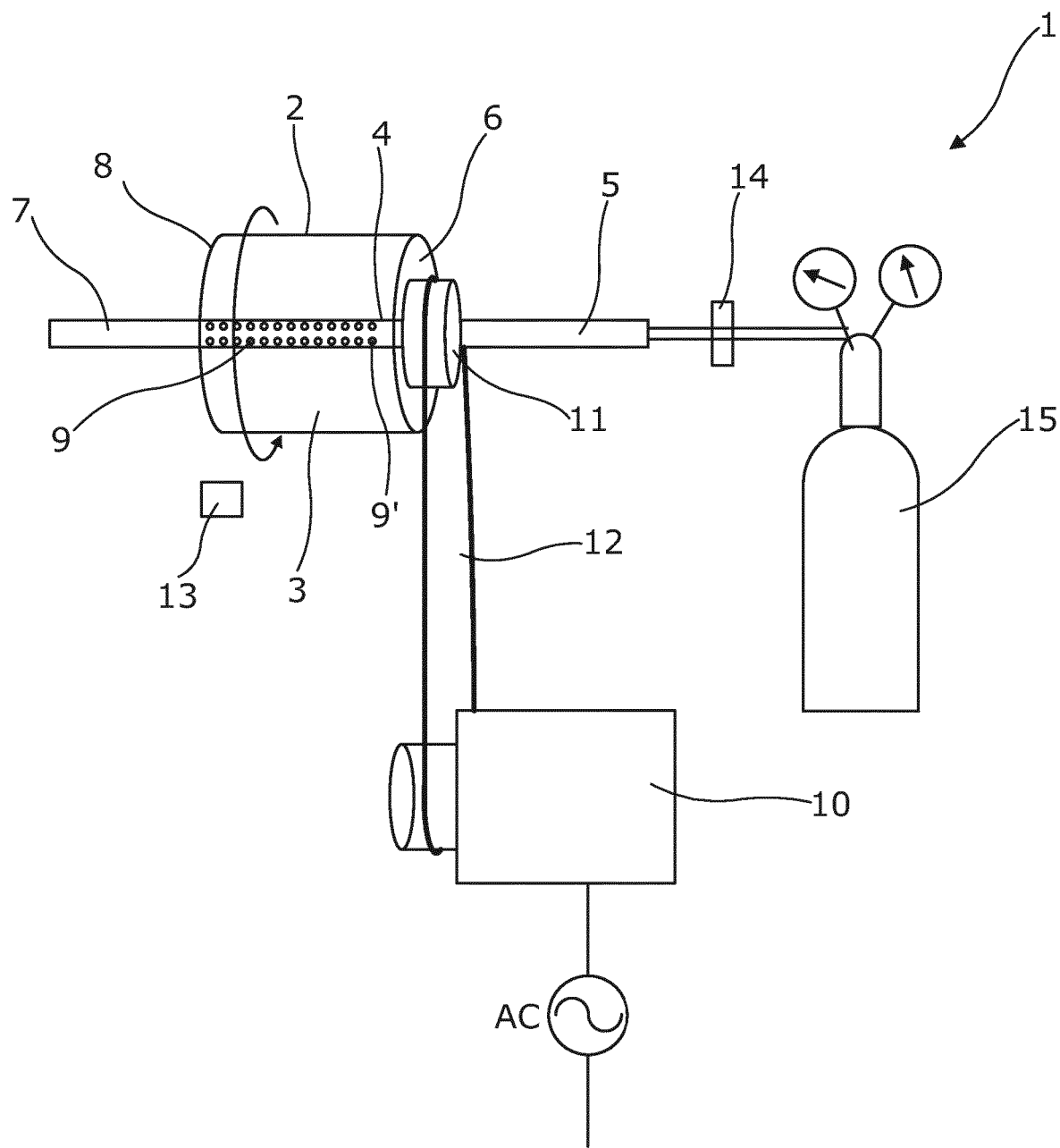
FIG. 1 shows a schematic representation of the apparatus described in WO2016/066462.

FIG. 1 the apparatus 1 for coating carrier particles with guest particles described in WO2016/066462. The apparatus comprises a cylindrical processing vessel 2 formed of acrylic or stainless steel (GMP grade) and having smooth inner walls. The vessel 2 is rotatable about its axis and has solid walls defining a chamber 3 having a volume of around 500 cm$^3$. A hollow shaft 4 formed of stainless steel extends within the chamber 3 along the axis of the vessel 2. The hollow shaft defines a gas flow path connected to a gas inlet 5 located at one axial end 6 of the vessel 2 and connected to a gas outlet 7 at the opposing axial end 8 of the vessel 2.

The hollow shaft 4 comprises four rows of axially aligned apertures 9 circumferentially-spaced around the shaft. The apertures 9 extend from the gas flow path within the hollow shaft 4 into the chamber 3.

The rows of apertures are selectively blockable so that during processing, one, two or three rows may be blocked.

The apertures 9 have an adjustable diameter to focus the gas flow into the chamber 3 and the apertures 9' towards the axial ends of the hollow shaft 4 include a respective flow director (not shown) which angles the gas flow towards the axial ends of the chamber 3.

The apparatus 1 further comprises a driving motor 10 for driving rotation of the vessel 2. The driving motor 10 is linked to a hub 11 affixed to axial end 6 of the vessel 2 adjacent the gas inlet 5 via a belt 12. The hollow shaft 4 passes through the axial centre of the hub 11.

The driving motor 10 is adapted to rotate the vessel 2 and hub 11 via the belt 12 at a speed of up to 4000 rpm. The driving motor includes a rotation sensor (not shown) for monitoring and maintaining the speed of rotation of the hollow shaft 4.

The apparatus 1 further comprises an infra-red temperature sensor 13 mounted externally of the chamber for monitoring the temperature within the chamber.

The apparatus 1 further comprises a pressure regulating system 14 for regulating the pressure within the chamber to ensure that there is no build-up of pressure within the chamber 3.

The rotation sensor, temperature sensor 13 and pressure regulating system 14 provide feedback to a computer system (not shown) running LabVIEW software or equivalent software.

The apparatus 1 further comprises a nitrogen source 15 connected to the gas inlet 5. The gas source 15 is adapted to provide nitrogen at a pressure of up to 80 psi e.g. between 20-80 psi at the gas inlet 5.

To use the apparatus 1, carrier particles and guest particles are placed within the chamber 3 of the vessel 2. These are introduced at either end of the chamber before the hollow shaft is fitted and sealed to the chamber (using stainless steel gaskets).

The carrier particles have a particle size of at least 5 times that of the guest particles (when measured using a laser diffraction particle size analyser which measure particle volume).

The gas inlet 5 is connected to the nitrogen gas supply 15.

The vessel 2 is rotated at a speed of up to 4000 rpm by the driving motor 10 and belt 12 which rotate the hub 11 which is affixed to the axial end 6 of the vessel 2.

As the vessel 2 rotates, the particles are subjected to centrifugal forces which force them towards the smooth inner surface of the walls of the vessel 2.

Nitrogen from the nitrogen source 15 flows to the gas inlet 5 and through the hollow shaft 4 along the gas flow path. The remainder of the gas passes into the chamber 3 through the four rows of apertures 9.

The gas passing though the apertures 9 will emanate in a radially outwards direction which will be coincident with the centrifugal force and thus will increase the collision force of the particles against the inner surface of the solid walls of the vessel. This, in turn, will increase the force with which the guest particles are adsorbed onto the carrier particles and thus will increase the adhesion between the two particles.

As the apertures 9 are in a row which extend axially along the hollow shaft 4, the air exiting the hollow shaft 4 will form axially-extending "air blades" which increase the shear forces applied to the particles and thus further increase adhesion between the particles.

Experimentation using fluticasone propionate and lactose monohydrate have been carried out as discussed below.

Example 1—Studies on Fluticasone Propionate/Lactose Monohydrate

Fluticasone Propionate is a potent glucocorticosteroid with anti-inflammatory action. It is used in inhalable drug formulations for the treatment of asthmatic patients for the suppression of inflammation within the airways. When delivered through the respiratory system using inhalation it requires only low doses and little fluticasone is absorbed into the systemic circulation hence reducing any side effects.

Lactose monohydrate is the most commonly used carrier excipient in dry powder inhaler formulations. It has the advantage of being highly investigated for its safety, stability and toxicity. It is compatible with multiple drugs and has relatively low price.

Content Uniformity for 0.5% DPI formulations

Fluticasone propionate/lactose monohydrate particles were produced using the coating apparatus described in WO2016/066462. The cylindrical processing vessel had a radius of 4.125 cm.

The formulations APT-1 to APT-4 were designed to deliver 50 μg of fluticasone propionate from 10 mg total dose.

The lactose monohydrate carrier particles were selected from two commercial brands: Respitose SV010 with average particle size of 95-125 μm and a D90 of 160-190 μm (where D90 is the particle size of 90% of the powder); and Respitose SV003 with average particle size of 60 μm and a D90 of 90 μm.

Fluticasone propionate was employed as guest particles in the form of a fine powder with average particle size of 1-6 μm.

The carrier and guest particles were added to the processing vessel. The processing conditions of the three prepared batches are depicted in Table-1.

TABLE 1

Example of DPI formulations with processing parameters

| Batch | Fluticasone Propionate (μg) | Total Dose (mg) | G-Force (g) | Gas pressure (bar) | Processing Time (min) | Guest % | Carrier |
|---|---|---|---|---|---|---|---|
| APT-1 | 50 | 10 | 190.4 | 0.38 | 30 | 0.5% | Respitose SV010 |
| APT-2 | 50 | 10 | 190.4 | 0.38 | 10 | 0.5% | Respitose SV010 |
| APT-3 | 50 | 10 | 107.1 | 0.38 | 10 | 0.5% | Respitose SV010 |
| APT-4 | 50 | 10 | 107.1 | 0.38 | 10 | 0.5% | Respitose SV003 |

Figure 2:
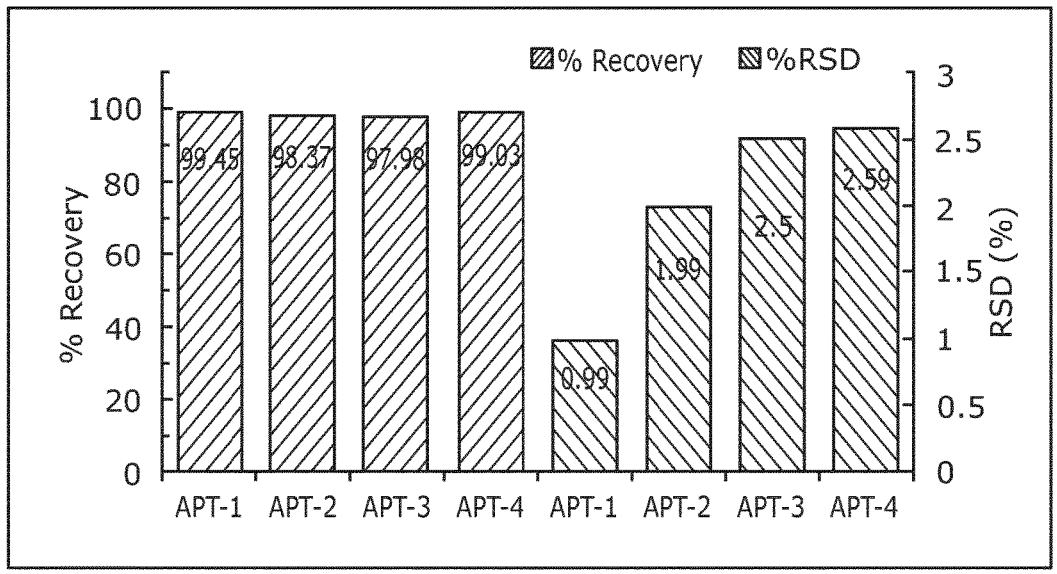
FIG. 2 shows the content uniformity and RSD of fluticasone propionate/lactose formulations.

Content uniformity of fluticasone propionate in the four batches was above 97% with low relative standard deviation (RSD) as shown in FIG. 2.

Uniformity was observed across all examples but a longer processing time and/or higher G-force was found to result in a higher level of homogeneity as evident from the RSD. Respitose SV010 with larger average particle size showed higher level of homogeneity compared to Respitose SV003 owing to the higher attraction force between the guest fluticasone particles and larger carrier particles.

Aerodynamic Performance of 0.5% DPI Formulations

Next, the aerodynamic performance of the four formulations using new generation impactor (NGI) apparatus form Copley Scientific was examined with the cut-off points in terms of aerodynamic particle diameter between 1-5 μm.

Individual samples of 10 mg were filled into 6 gelatine capsules (size 3) and then discharged into the NGI using Aerolizer™ DPI device.

The air flow rate was set at 60 L/min for 4 sec to mimic 4 L of inhaled air during human inhalation process. The emitted fraction was calculated based on the percentage of recovered and HPLC analysed fluticasone from the mouth piece, induction tube, pre-separator and stages 1-8.

Figure 3:
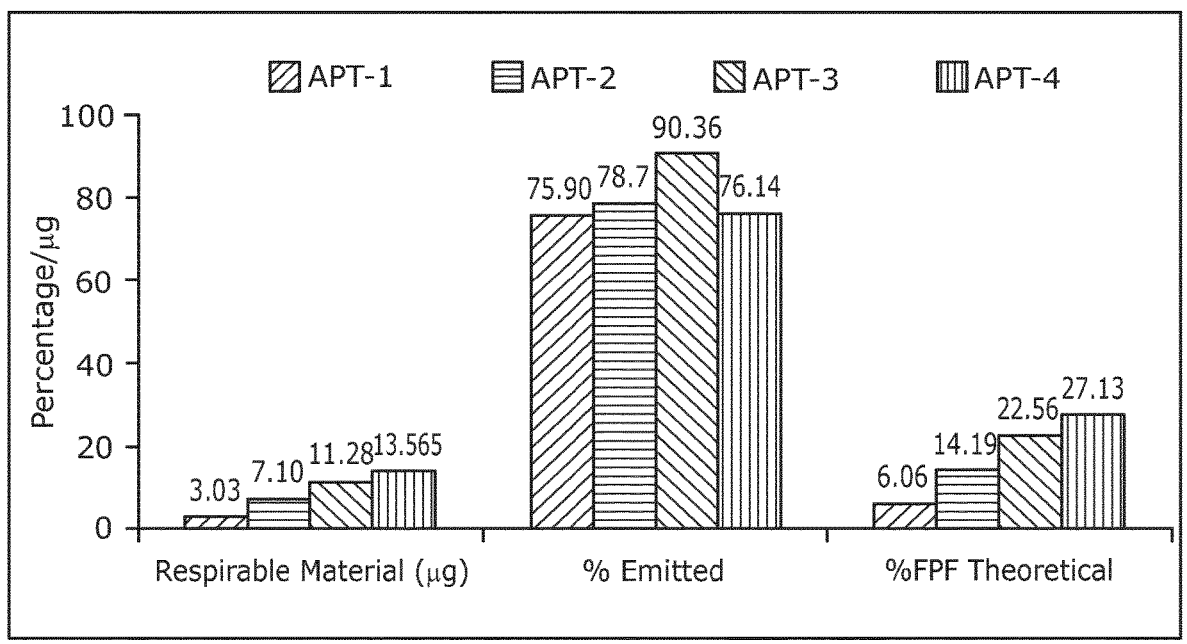
FIG. 3 shows the amount of respirable fine particles collected and percentage emitted dose for the fluticasone propionate/lactose formulations.

The amount of respirable fine particles is the sum of recovered dose within the cut-off aerodynamic diameter, whereas the fine particle fraction (FPF) is the percentage of the recovered dose within the cut-off aerodynamic diameter of 1-5 μm to the theoretical dose. Results are shown in FIG. 3.

The results show the ability of the designed process parameters (G-force) and input parameters (carrier particle size) to deliver various amounts of respirable fine particles that ranges from 3-13 μg representing a tailored FPF (6-27% w/w) and emitted dose.

The produced formulation showed high degree of emitted dose owing to the excellent flowability of the powder. It is noted that process optimisation can result in targeted FPF % without jeopardising content uniformity and blend homogeneity.

Example 2—Content Uniformity for 0.71% DPI Formulations

Experiments were carried out using higher concentration of fluticasone propionate to deliver 100 μg from 14 mg total dose (0.71%) using the apparatus of WO2016/066462.

Processing parameters are listed in Table 2 below.

TABLE 2

Example of DPI formulations with processing parameters for batch size of 20 g

| Batch | Fluticasone Propionate (μg) | Total Dose (mg) | G-Force (g) | Gas pressure (bar) | Processing Time (min) | Guest % | Carrier |
|---|---|---|---|---|---|---|---|
| APT-5 | 100 | 14 | 107.1 | 0.38 | 10 | 0.71% | Respetose SV010 |
| APT-6 | 100 | 14 | 107.1 | 0.38 | 10 | 0.71% | Respetose SV003 |
| APT-7 | 100 | 14 | 107.1 | 0.38 | 30 | 0.71% | Respetose SV003 |
| APT-8 | 100 | 14 | 190.4 | 0.38 | 10 | 0.71% | Respetose SV003 |
| APT-9 | 100 | 14 | 190.4 | 0.38 | 10 | 0.71% | Respetose SV003 |
| APT-10 | 100 | 14 | 190.4 | 0.38 | 8.3 | 0.71% | Respetose SV010 |
| APT-11 | 100 | 14 | 84.6 | 0.38 | 5 | 0.71% | Respetose SV010 |
| APT-12 | 100 | 14 | 107.1 | 0.38 | 10 | 0.71% | Respetose SV003 |

Figure 4:
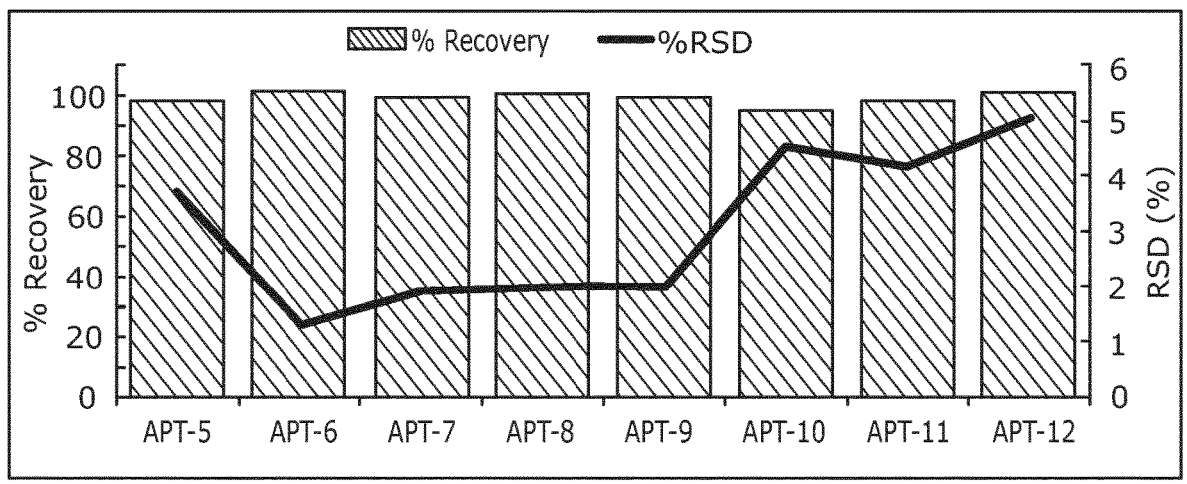
FIG. 4 shows the content uniformity and RSD of further fluticasone propionate/lactose formulations.

As shown in FIG. 4, content uniformity was high for all formulations with low RSD for all batches APT-5-APT-12.

Aerodynamic Performance of 0.71% DPI Formulations

Figure 5:
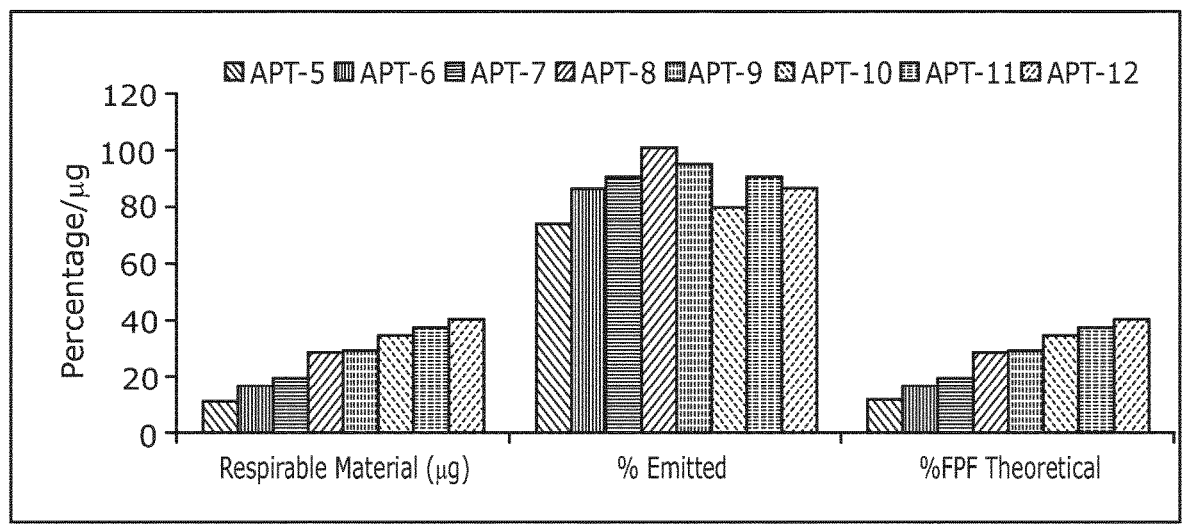
FIG. 5 shows the amount of respirable fine particles collected and percentage emitted dose for the further fluticasone propionate/lactose formulations.

The results for 100 μg fluticasone DPI formulations can be seen in FIG. 5 which shows the ability of the process to be engineered to deliver various percentages of FPF and emitted doses resulting from the degree of adherence/detachment whilst maintaining tight control on content uniformity.

Results show that FPF as high as 40% could be achieved. The emitted dose could reach 100% as is the case with formulation APT-8.

Scanning Electron Microscopy (SEM) Images of Selected Formulations

Figure 6:
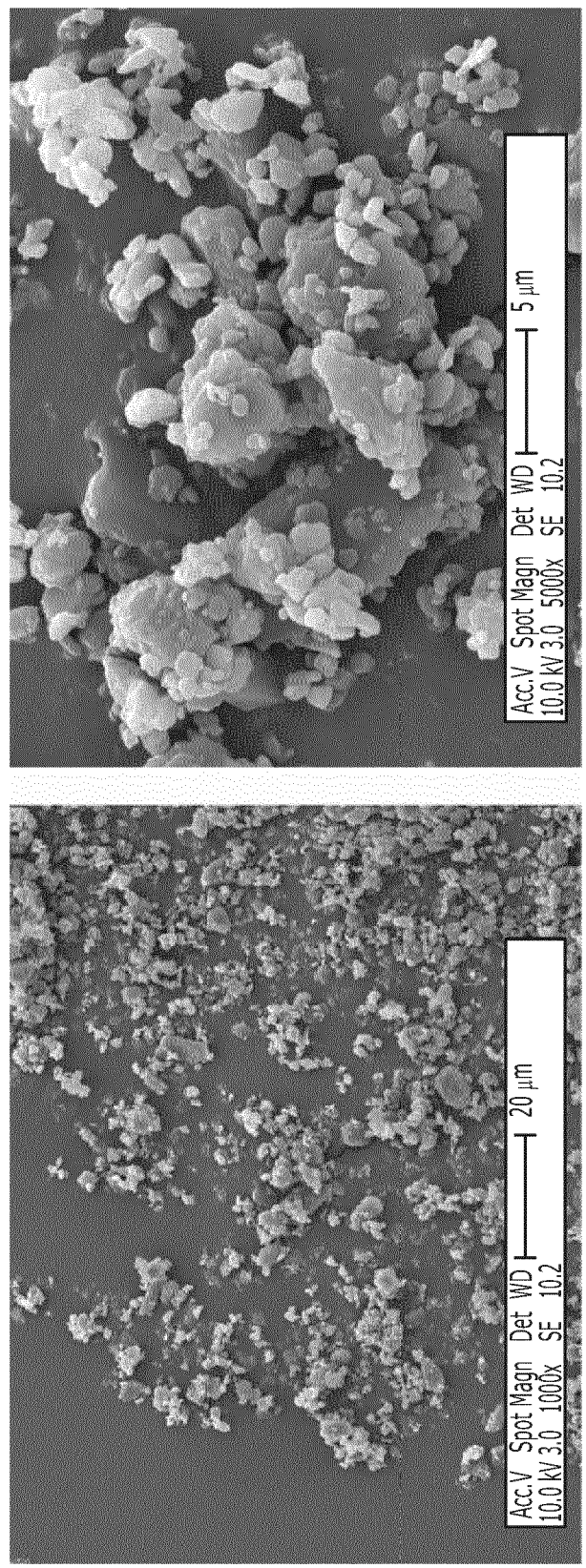
FIG. 6 shows SEM images of fluticasone propionate and sample formulations.
Figure 6:
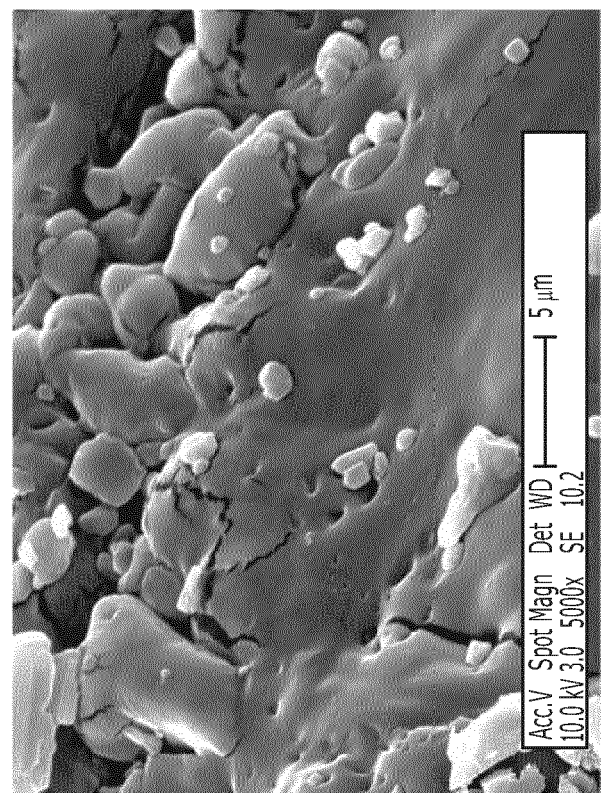
Figure 6:
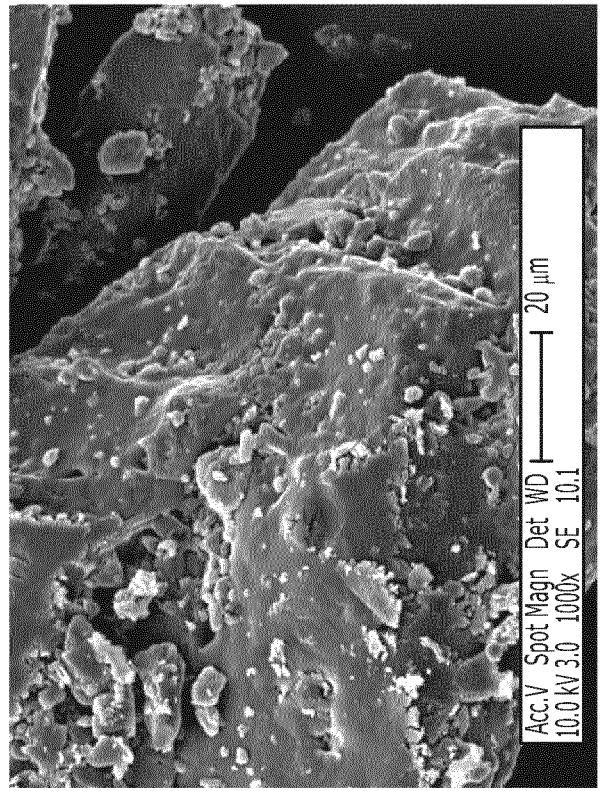
Figure 6:
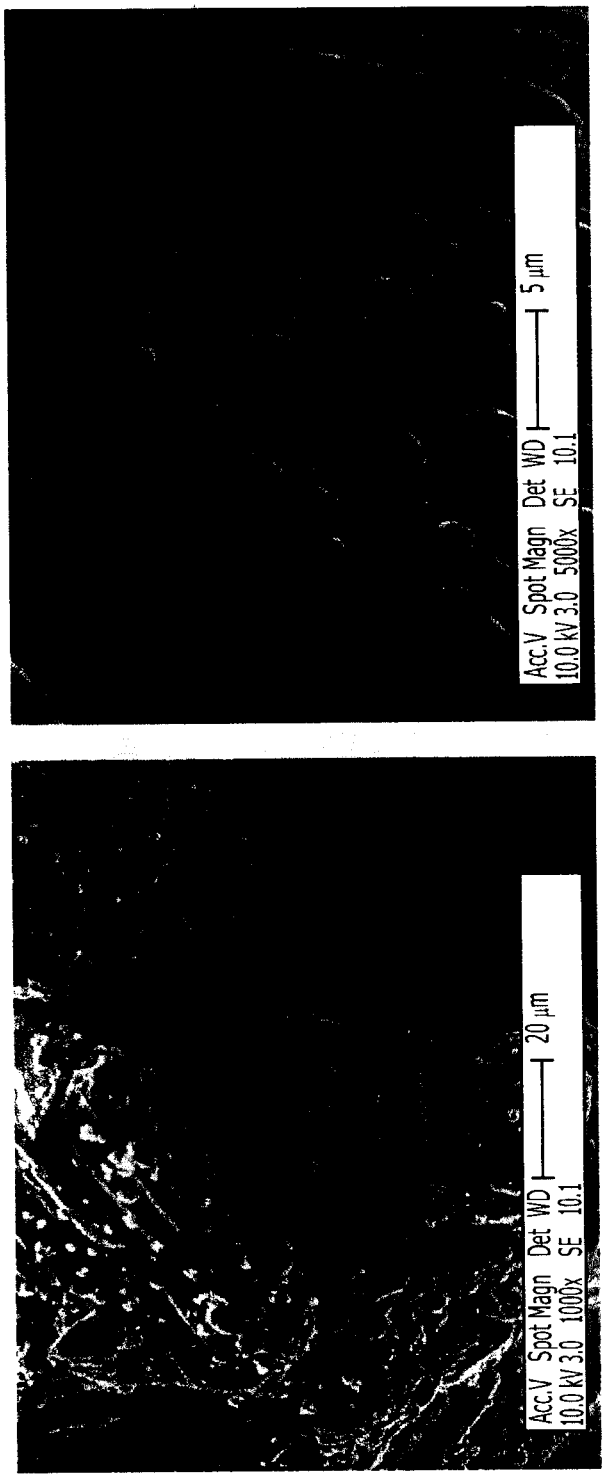

FIG. 6 shows SEM images of the surface of (A) fluticasone propionate particles with average particle size of ranging from 1-5 μm. The images at 1000× and 5000× magnification show the fine particles are agglomerated. FIGS. 6B-D show the distribution of the fluticasone propionate on the surface of the lactose monohydrate carrier after processing using the process described herein. It should be noted that the degree of distribution and deagglomeration of the fluticasone propionate increases with the reduction in FPF (B formulation has high degree of homogeneity and distribution resulting in a FPF of around 6%, C formulation had FPF of 22.6% whereas D formulation had FPF of 29.1%).

Example 3—Micronized Carbamazepine Guest Particles on Polyvinylpyrrolidone Carrier Particles Carbamazepine/polyvinylpyrrolidone dry coated functionalised particles were produced using the apparatus of WO2016/066462.

Various formulations of the carbamazepine and polyvinylpyrrolidone (PVP) (Kollidon K25) were manufactured. PVP was used as the carrier particle with an average particle size of approximately 59 μm and D90 of 102 μm. Carbamazepine was employed as a model poorly soluble drug in a micronized state to act as the guest particle, with an average particle size of 5 μm and a D90 of 11.16 μm. Mixing conditions were fixed at 190.4 g, 0.38 bar of gas pressure and a mixing times varying from 30 to 60 mins.

Figure 7:
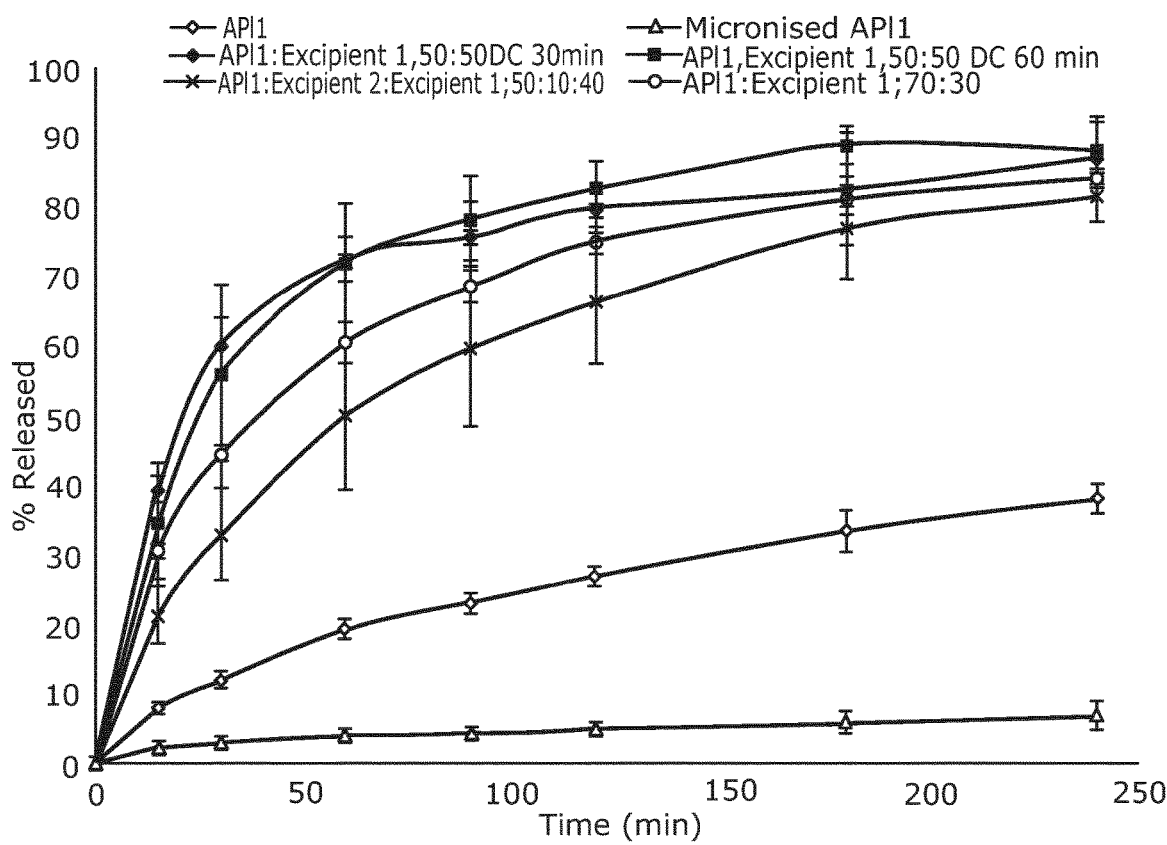
FIG. 7 shows the dissolution/time profile for dry coated carbamazepine formulations against control highlighting improved dissolution of the drug post dry coating.

The dissolution rate was analysed using standard USP II dissolution apparatus using the basket assembly dissolution vessels. Standard 200 mg dose powders were investigated to mimic a patient dose, with dissolution conditions maintained at 37° C. and the basket apparatus rotated at 50 rpm in distilled water. Powders were placed in the basket and submerged in to the dissolution apparatus and ran over 4 h. Samples were taken at predetermined time intervals, with each sample volume replaced with the same amount of fresh dissolution media to maintain sink conditions. The samples were filtered appropriately and analysed for drug content using HPLC apparatus at each of the time points. All results were taken in triplicate, and are represented in FIG. 7.

Results showed an enhanced dissolution rate, and enhanced maximum dissolution for processed powders when compared to off the shelf carbamazepine and micronized carbamazepine. All dry coated powders displayed an improved dissolution behaviour at different concentrations of solubility/dissolution controlling polymer (PVP) as well as different processing times. The 50:50 formulation mixed for 60 mins provided the most beneficial behaviour with almost 90% drug release of a poorly soluble drug over the 4 h time period, highlighting a 130% improvement in drug dissolution rate when compared to the off the shelf drug. All other formulations showed a similarly high improvement in drug dissolution highlighting the ability of the technology to control and enhance the dissolution rate of low soluble drugs.

The micronized carbamazepine showed a very poor release due to agglomeration of the particles, decreasing the surface area for wettability. The inventive process allowed uniform distribution of the drug through the carrier with uniformity of content being >98%, allowing thorough wetting of the drug particles as well as an increased dissolution rate. The process does not generate any heat or use any solvents so is ideal for unstable drugs, and with 70% of new chemical entities being poorly soluble this method of processing for solubility/dissolution control/enhancement presents an ideal solution to improve drug dissolution rate.

Example 4—Micronised Piroxicam Guest Particles on Polyvinylpyrrolidone Carrier Particles Piroxicam/PVP dry coated functionalised particles were produced using the apparatus of WO2016/066462.

Various formulations of the piroxicam and PVP (Kollidon K25) were manufactured. PVP was used as the carrier particle with an average particle size of approximately 59 μm and D90 of 102 μm. Piroxicam was employed as a model poorly soluble drug in a micronized state to act as the guest particle, with an average particle size of 3.36 μm and a D90 of 6.98 μm. Mixing conditions were fixed at 190.4 g, 0.38 bar of gas pressure and a mixing time of 30 mins.

Figure 8:
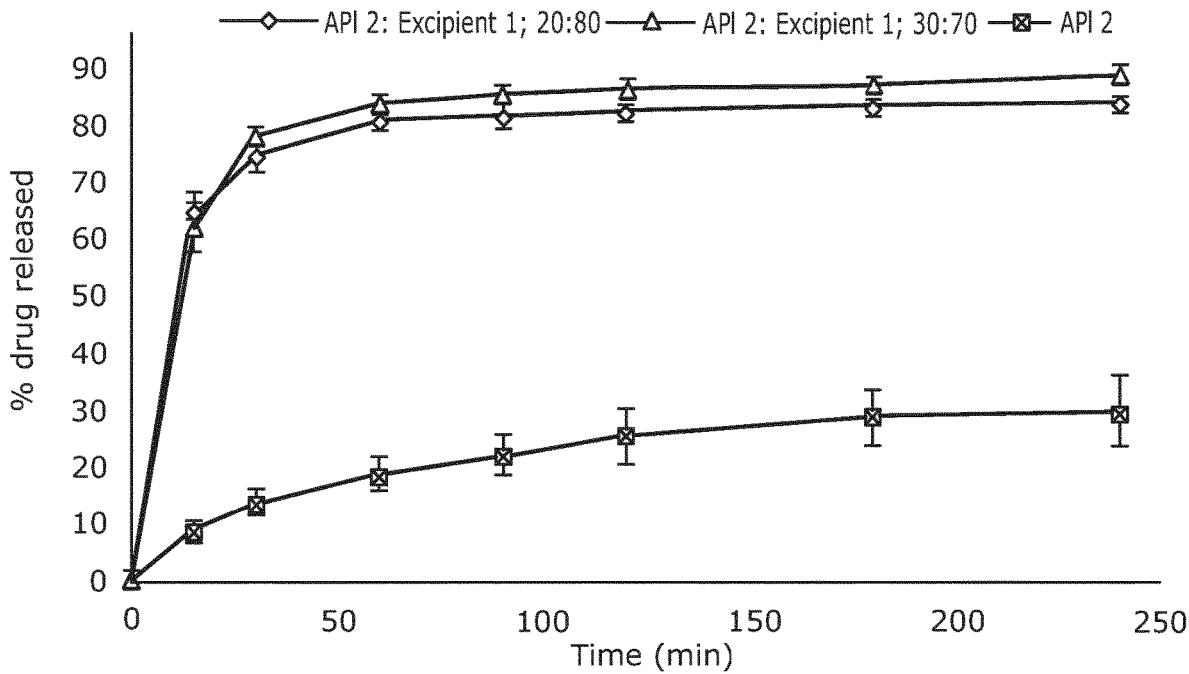
FIG. 8 shows the dissolution/time profile for piroxicam/PVP formulations against control highlighting improved dissolution of the drug post dry coating.

The dissolution rate was analysed using standard USP II dissolution apparatus using the basket assembly dissolution vessels. Standard 20 mg dose powders were investigated to mimic a patient dose, with dissolution conditions maintained at 37° C. and the basket apparatus rotated at 50 rpm in 0.1N hydrochloric acid. Powders were placed in the basket and submerged in to the dissolution apparatus and ran over 4 h. Samples were taken at predetermined time intervals, with each sample volume replaced with the same amount of fresh dissolution media to maintain sink conditions. The samples were filtered appropriately and analysed for drug content using HPLC apparatus at each of the time points. All results were taken in triplicate, and are represented in FIG. 8.

Results showed an enhanced dissolution rate as well as a vastly improved maximum dissolution at the end of the 4 h interval compared to the control piroxicam alone. Both concentrations of rate controlling polymer (PVP) highlighted an improved dissolution behaviour with the 70% PVP showing the most beneficial performance. This formulation indicated 88.5% drug release compared to the control formulation showing a 29.7% release which amounted to a 197% increase in overall dissolution. A similar behaviour was observed with the 80% PVP formulation highlighting that the technology gives the ability to control and improve the dissolution behaviour through its advantageous processing conditions.

Example 5—Micronised Phenytoin Guest Particles on Polyvinylpyrrolidone Carrier Particles Phenytoin/PVP dry coated functionalised particles were produced using the apparatus of WO2016/066462.

Various formulations of the phenytoin and PVP (Kollidon K25)/micronised sodium lauryl sulfate were manufactured. PVP was used as the carrier particle with an average particle size of approximately 59 μm and D90 of 102 μm. Piroxicam was employed as a model poorly soluble drug in a micronized state to act as the guest particle, with an average particle size of 11.44 μm and a D90 of 19.05 μm. Mixing conditions were fixed at 190.4 g, 0.38 bar of gas pressure and a mixing time of 30 mins.

Figure 9:
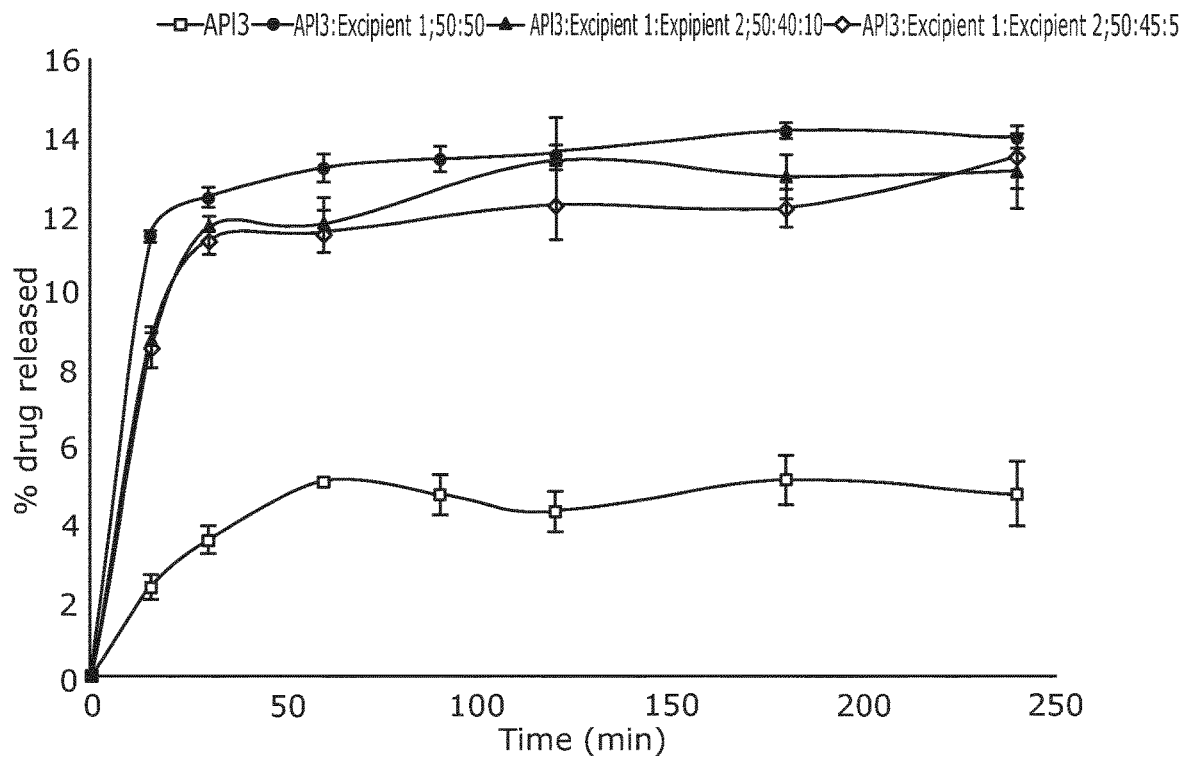
FIG. 9 shows the dissolution/time profile for phenytoin/PVP formulations against control highlighting improved dissolution of the drug post dry coating.

The dissolution rate was analysed using standard USP II dissolution apparatus using the basket assembly dissolution vessels. Standard 200 mg dose powders were investigated to mimic a patient dose, with dissolution conditions maintained at 37° C. and the basket apparatus rotated at 50 rpm in distilled water. Powders were placed in the basket and submerged in to the dissolution apparatus and ran over 4 h. Samples were taken at predetermined time intervals, with each sample volume replaced with the same amount of fresh dissolution media to maintain sink conditions. The samples were filtered appropriately and analysed for drug content using HPLC apparatus at each of the time points. All results were taken in triplicate, and are represented in FIG. 9.

Results from the three processed formulations highlighted an improved dissolution rate alongside a higher maximum dissolution over the control phenytoin formulation. The 50:50 PVP/phenytoin formulation displayed the most improved dissolution behaviour with a 14% release, compared to the 4.7% release of the phenytoin alone. This amounted to approximately 197% increase in maximum dissolution. A similar increase was observed with the sodium lauryl sulfate/PVP combinations highlighting that the process could be tailored with excipients and processing parameters to deliver control of the drug dissolution profile to improve and tailor the release of the drug.

Example 6—Micronized Sodium Lauryl Sulphate Guest Particles on Carbamazepine Carrier Particles Carbamazepine/sodium lauryl sulphate functionalised particles were produced using the apparatus of WO2016/066462.

The primary formulation comprised 25 wt % sodium lauryl sulphate with 75 wt % carbamzaepine, with a second formulation produced using 12.5 wt % sodium lauryl sulphate and 87.5% carbamazepine.

Off the shelf carbamazepine was used with an average particle size of approximately 91 μm and D90 of 156 μm. Sodium lauryl sulphate was employed in a micronized state as the guest particle, with an average particle size of 8 μm and a D90 of 15.6 μm.

Mixing conditions were fixed at a G force of 190.4 g, 0.38 bar of gas (nitrogen) pressure and a mixing time of 30 mins.

Results indicated that dry coating carbamazepine with the micronized sodium lauryl sulphate enhanced dissolution rate, and maximum dissolution of carbamazepine when compared to the carbamazepine control.

Figure 10:
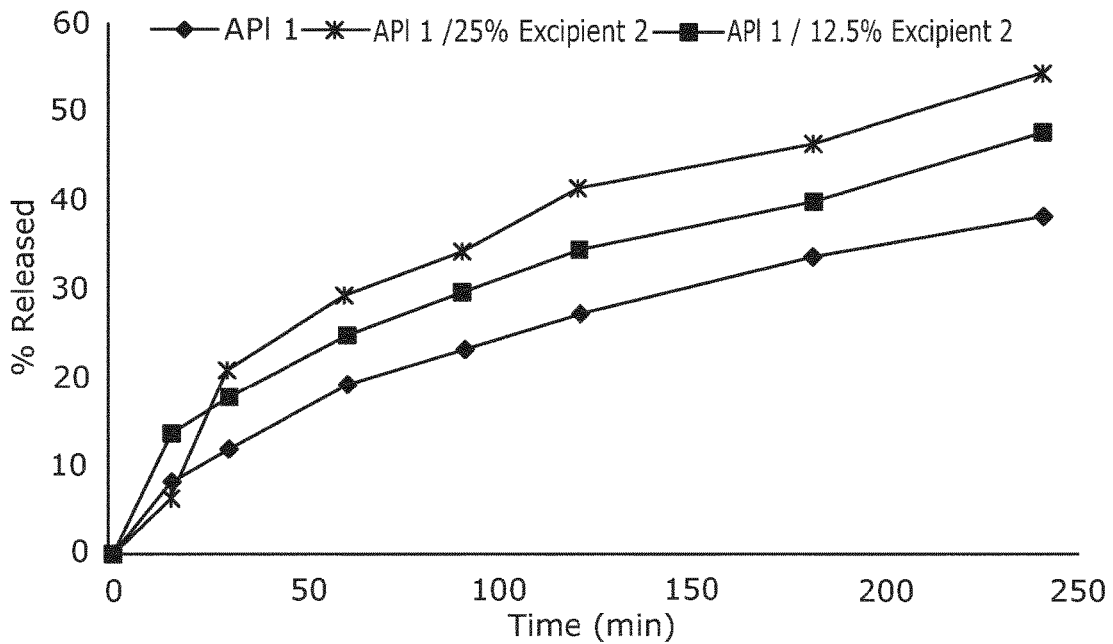
FIG. 10 shows the dissolution/time profile for carbamazepine/SLS formulations against control highlighting improved dissolution of the drug post dry coating.

As can be seen in FIG. 10, APT formulation 2 showed around 54% drug release of the model insoluble drug carbamazepine and APT formulation 3 showed around 48% drug release compared to off the shelf carbamazepine (CBZ), which showed around 38% drug release, highlighting a 42% and 25% improvement in drug dissolution rate for APT formulation 2 and 3 respectively.

The process results in dissolution rate improvement and allowed uniform distribution of the drug through the carrier with uniformity of content being >98%, allowing thorough wetting of the drug particles as well as an increased dissolution rate.

The process does not require micronisation of the drug particle making it ideal for drugs which have physical instabilities. The lack of heat generation in the process, as well as absence of solvent makes this method ideal for unstable drugs.

Example 7—Micronised Dissolution Rate Controlling Guest Polymers on Carbamazepine Carrier Particles Carbamazepine/dissolution rate controlling guest polymers were processed using the apparatus of WO2016/066462.

Figure 11:
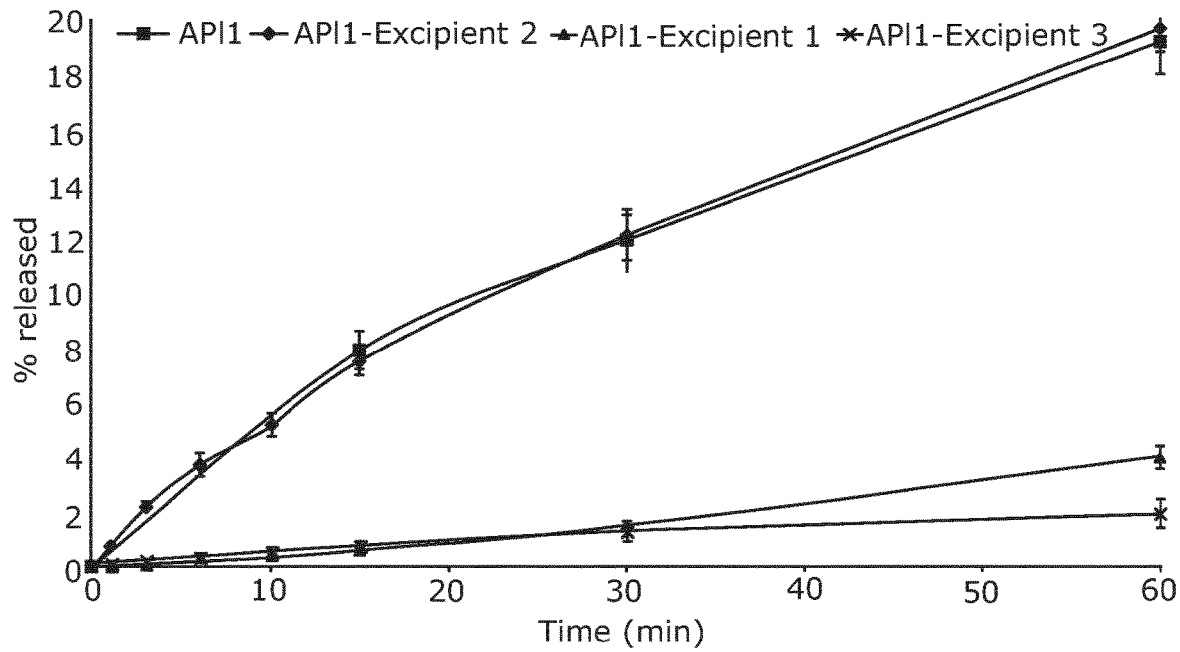
FIG. 11 shows the dissolution time profile for carbamazepine with different polymers used to control the rate of drug dissolution.

Binary mixtures of drug and dissolution rate controlling guest polymers were manufactured at various concentrations to produce a coating that would tailor/control the dissolution rate of the drug, as displayed in FIG. 11. This demonstrated the flexibility of the process to use different materials to alter the drug release to desired levels. Off the shelf carbamazepine was mixed with three different rate controlling polymers; poly(ethylene) oxide of high viscosity (excipient 1), poly(ethylene) of low viscosity (excipient 2) and ethylcellulose (excipient 3).

Mixing conditions were fixed at a G force of 190.4 g, 0.38 bar of gas (nitrogen) pressure and a mixing time of 60 mins.

Results indicated that the choice of rate controlling polymer could tailor the release of the drug to either match the release of the drug itself, as observed with excipient 2, or the release of the drug could be slowed/inhibited to very low levels over the 60 min time interval, with excipient 1 showing 4% release and excipient 3 displaying a 1.9% release. Low levels of drug release could be deemed useful for applications such as masking the odour/taste of the drug, as a low drug release would inhibit contact of the drug with the taste buds and therefore increase the palatability of the formulation.

Figure 12:
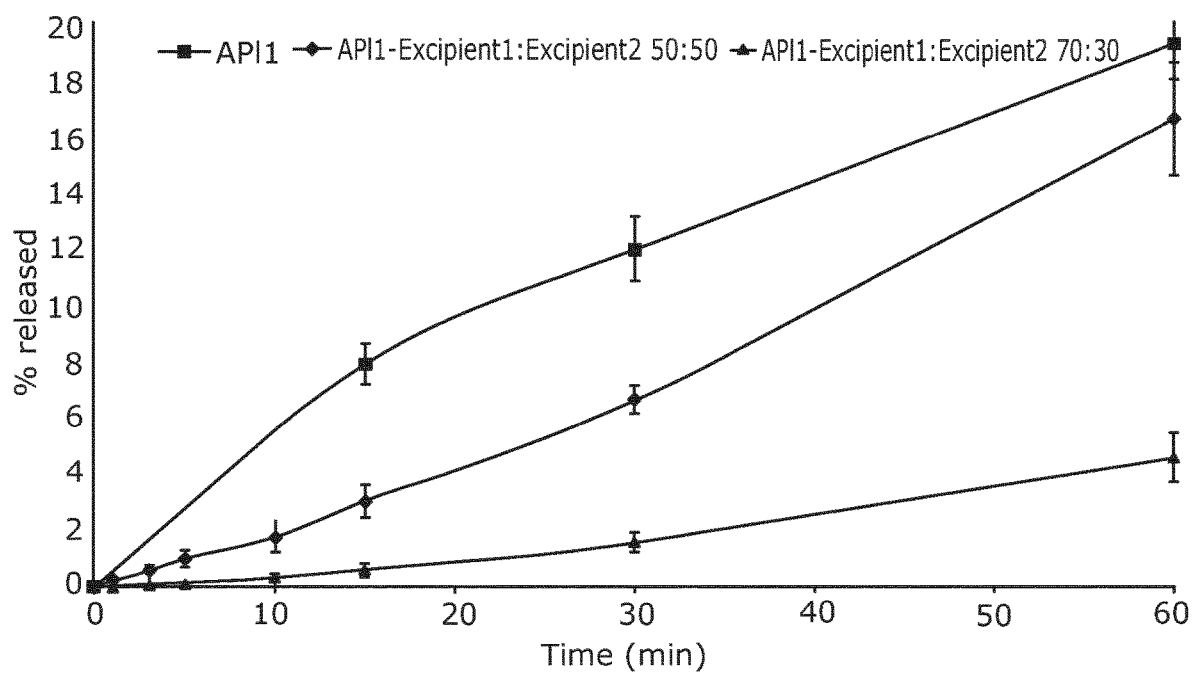
FIG. 12 shows the dissolution time profile of Carbamazepine with varying combinations of two rate controlling polymers to tailor the rate of drug dissolution.

FIG. 12 uses combinations of two of these dissolution rate controlling polymers with carbamazepine, to tailor the release profile to achieve a desired drug release. Excipients 1 and 2 were chosen as they are different viscosity grades of poly(ethylene) oxide and they gave opposite dissolution profiles. As can be seen from FIG. 12, changing the combination of the two rate controlling polymers allowed tailoring of the release profile to achieve a different release after the 60 min time period. The 50:50 combination displayed a total release similar to the drug alone, however the release of the drug was suppressed in the first 10 mins, which would be an ideal profile for a taste masked formulation, whereby release should be minimum in the initial 5-10 mins and then should increase similar to the drug alone. When the concentration of the high viscosity poly(ethylene) oxide was increased the dissolution profile was further suppressed, suggesting the dissolution could be tailored using the technology and different combinations of polymers.

Example 8—Micronised Dissolution Rate Controlling Guest Polymers on Flucloxacillin Sodium Carrier Particles Flucloxacillin sodium/dissolution rate controlling guest polymers were processed using the apparatus of WO2016/066462.

Figure 13:
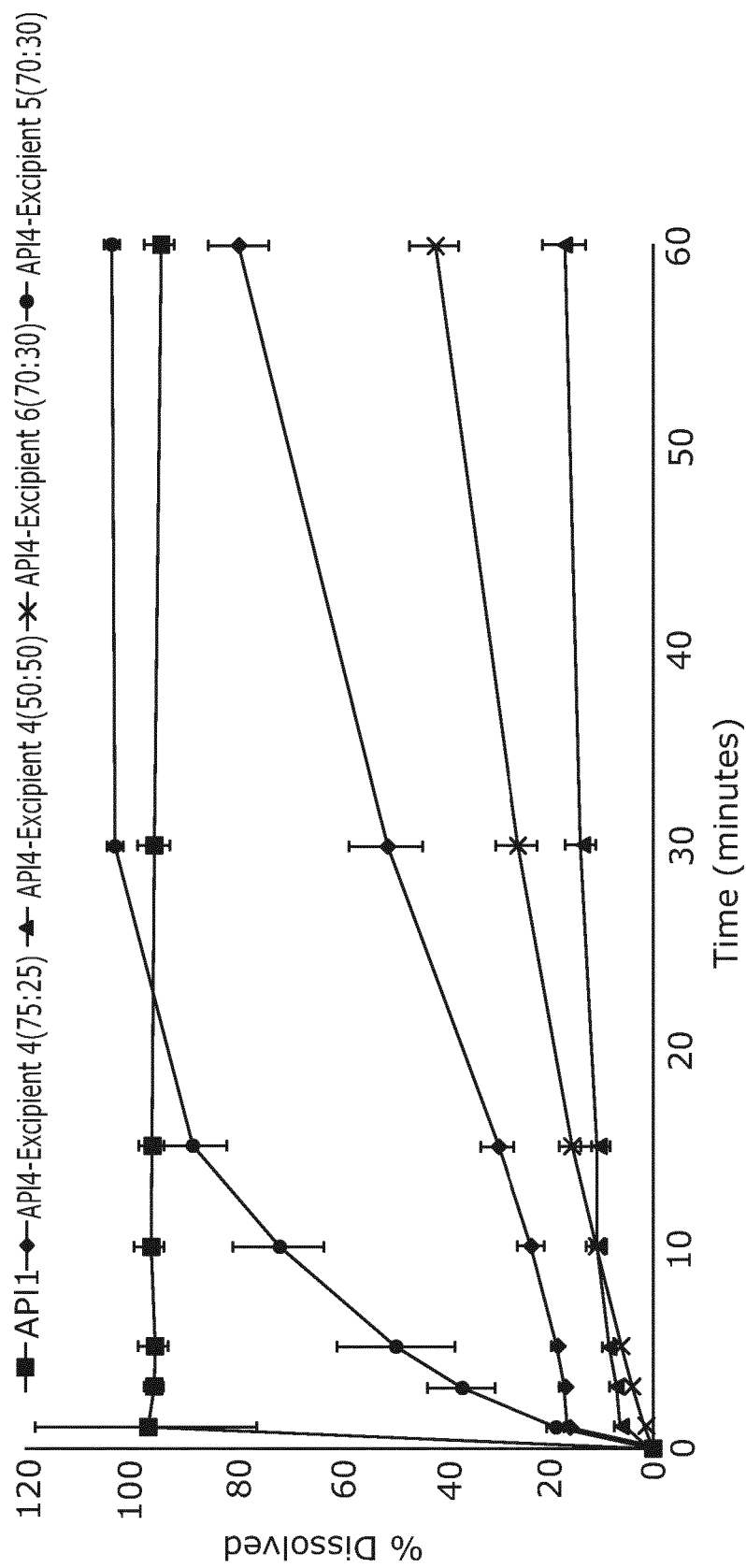
FIG. 13 shows the dissolution/time profile of flucloxacillin Sodium with various rate controlling polymers to control the rate of drug dissolution

Binary mixtures of drug and dissolution rate controlling guest polymers were manufactured at various concentrations to produce a coating that would tailor/control the dissolution rate of the drug, as displayed in FIG. 13. This was to demonstrate flexibility of the process to use highly soluble drugs, such as flucloxacillin sodium alongside low soluble drugs such as carbamazepine. Off the shelf flucloxacillin sodium was mixed with three different rate controlling polymers; poly(ethylene) oxide of high viscosity (excipient 5), poly(ethylene) of low viscosity (excipient 3) and ethylcellulose (excipient 6).

The dissolution rate was analysed using standard USP II dissolution apparatus using the basket assembly dissolution vessels. Standard 250 mg dose powders were investigated to mimic a patient dose, with dissolution conditions maintained at 37° C. and the basket apparatus rotated at 50 rpm in pH 6.8 phosphate buffer. Powders were placed in the basket and submerged in to the dissolution apparatus and ran over 60 mins. Samples were taken at predetermined time intervals, with each sample volume replaced with the same amount of fresh dissolution media to maintain sink conditions. The samples were filtered appropriately and analysed for drug content using HPLC apparatus at each of the time points. All results were taken in triplicate, Mixing conditions were fixed at a G force of 190.4 g, 0.38 bar of gas (nitrogen) pressure and a mixing time of 60 mins.

FIG. 13 highlights results from the flucloxacillin sodium binary mixtures coated with the different dissolution rate controlling polymers. Again, it can be seen that different rate controlling polymers can alter the release profile of the drug that slows/inhibits its release. In this case, flucloxacillin sodium is very soluble, and exhibits full release within a minute when assessed alone. The data presented here shows that all dissolution rate controlling polymers slow the release of the drug at varying levels. Also, the data presented different concentrations of excipient 4, and that increasing the amount of guest excipient on to the surface of the flucloxacillin sodium slowed the release of the drug further, as a more significant coating is achieved.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the scope of the invention as defined in the claims.

All references referred to above are hereby incorporated by reference.

The invention claimed is:

1. A process for coating carrier particles with guest particles, the process comprising:
    providing an apparatus comprising a processing vessel having solid walls defining a chamber for receiving said particles, and a hollow shaft extending within said chamber at least partly along the axis of rotation of the cylindrical processing vessel, the hollow shaft defining a gas flow path connected to a gas inlet, and having one or more axially-extending slots or one or more axially-extending rows of apertures allowing fluid communication between the gas flow path and the chamber;
    adding the particles to the chamber; and
    rotating the cylindrical processing vessel about an axis to impart a centrifugal (G) force of between 10 and 2100 g on the particles whilst flowing gas from the gas inlet along the gas flow path in the hollow shaft and into the chamber, in a radially-outwards direction, through the one or more axially-extending slots or one or more axially-extending rows of apertures to reinforce the centrifugal force, wherein the guest particles comprise an inhalable drug, and the gas is flowed from the gas inlet at a flow rate of between 1 and 75 L/min to cause de-agglomeration then adherence of the guest particles on the carrier particles.

2. A process according to claim 1 comprising rotating the cylindrical processing vessel about an axis to impart a centrifugal (G) force of between 10-2000 g.

3. A process according to claim 1 comprising rotating the cylindrical processing vessel at a speed between 250-4000 rpm.

4. A process according to claim 1 comprising rotating the cylindrical processing vessel for up to 180 minutes.

5. A process according to claim 1 wherein the mean particle size of the inhalable drug guest particle is between 1-6 micrometres measured using a laser diffraction particle size analyser that measures on a by volume basis.

6. A process according to claim 5 wherein the mean particle size of the guest particles is greater than 50 nanometres measured using a laser diffraction particle size analyser that measures on a volume basis.

7. A process according to claim 1 wherein the carrier particle size is equal or greater than 5 times the mean particle size of the inhalable drug guest particles.

8. A process according to claim 7 wherein the carrier particle size is equal to or greater than 5 micrometres.

9. A process for coating carrier particles with guest particles, the process comprising:
providing an apparatus comprising a processing vessel having solid walls defining a chamber for receiving said particles and a hollow shaft extending within said chamber at least partly along the axis of rotation of the cylindrical processing vessel, the hollow shaft defining a gas flow path connected to a gas inlet, and having one or more axially-extending slots or one or more axially-extending rows of apertures allowing fluid communication between the gas flow path and the chamber to reinforce the centrifugal force;
adding the particles to the chamber; and
rotating the cylindrical processing vessel about an axis to impart a centrifugal (G) force on the particles while flowing gas from the gas inlet along the gas flow path in the hollow shaft and into the chamber, in a radially-outwards direction, through the one or more axially-extending slots or one or more axially-extending rows of apertures,
wherein one of the carrier particles and the guest particles comprises a material having a solubility/dissolution and the other comprises a solubility/dissolution controlling agent,
wherein the solubility/dissolution controlling agent comprises an anionic surfactant, a cationic surfactant, a non-ionic surfactant, a zwitterionic (amphoteric) surfactant, an amino acid, a disintegrant, a water insoluble moiety, a water-soluble moiety or a combination of any of the above, and the gas is flowed from the gas inlet at a flow rate of between 1 and 75 L/min to cause de-agglomeration then adherence of the guest particles on the carrier particles.

10. A process according to claim 9 wherein the mean particle size of the guest particle is between 0.2 and 38 micrometres measured using a laser diffraction particle size analyser that measures particle volume.

11. A process according to claim 9 wherein the carrier particle size is equal or greater than 5 times the mean particle size of the guest particles.

12. A process according to claim 11 wherein the carrier particle size is equal to or greater than 5 micrometres.

13. A process according to claim 9 comprising providing an apparatus further comprising a hollow shaft extending within said chamber at least partly along the axis of rotation of the cylindrical processing vessel, the hollow shaft defining a gas flow path connected to a gas inlet, and having one or more axially-extending slots or one or more axially-extending rows of apertures allowing fluid communication between the gas flow path and the chamber, and flowing gas from the gas inlet along the gas flow path in the hollow shaft and into the chamber through the one or more axially-extending slots or one or more axially-extending rows of apertures.

14. A process for coating carrier particles with guest particles, the process comprising:
providing an apparatus comprising a processing vessel having solid walls defining a chamber for receiving said particles and a hollow shaft extending within said chamber at least partly along the axis of rotation of the cylindrical processing vessel, the hollow shaft defining a gas flow path connected to a gas inlet, and having one or more axially-extending slots or one or more axially-extending rows of apertures allowing fluid communication between the gas flow path and the chamber;
adding the particles to the chamber; and
rotating the cylindrical processing vessel about an axis to impart a centrifugal (G) force on the particles while flowing gas from the gas inlet along the gas flow path in the hollow shaft and into the chamber, in a radially-outwards direction, through the one or more axially-extending slots or one or more axially-extending rows of apertures to reinforce the centrifugal force,
wherein one of the carrier particles and the guest particles comprises a drug and the other comprises a solubility/dissolution controlling agent;agent,
the solubility/dissolution controlling agent comprises an anionic surfactant, a cationic surfactant, a non-ionic surfactant, a zwitterionic (amphoteric) surfactant, an amino acid, a disintegrant, a water insoluble moiety, a water-soluble moiety or a combination of any of the above, and
the gas is flowed from the gas inlet at a flow rate of between 1 and 75 L/min to cause de-agglomeration then adherence of the guest particles on the carrier particles.

* * * * *